United States Patent [19]

Cohen

[11] Patent Number: 5,330,457
[45] Date of Patent: Jul. 19, 1994

[54] ENHANCED CORE UTILIZATION IN ABSORBENT PRODUCTS

[75] Inventor: Richmond R. Cohen, Hockessin, Del.

[73] Assignee: Hercules Incorporated, Wilmington, Del.

[21] Appl. No.: 941,856

[22] Filed: Sep. 8, 1992

Related U.S. Application Data

[63] Continuation of Ser. No. 768,785, Sep. 30, 1991, abandoned.

[51] Int. Cl.$^5$ .............................................. A61F 13/15
[52] U.S. Cl. .................................. 604/378; 604/358; 604/367; 604/368; 604/370; 604/375; 604/379
[58] Field of Search .................... 428/361, 364, 391; 604/358, 367–368, 370, 375, 378, 379, 385.1

[56] References Cited

U.S. PATENT DOCUMENTS

| | | | |
|---|---|---|---|
| 2,668,785 | 2/1954 | Jefferson et al. | 428/361 |
| 2,751,962 | 6/1956 | Drummond . | |
| 2,983,625 | 5/1961 | Schappel | 428/361 |
| 3,388,028 | 6/1968 | Alexander | 428/364 |
| 3,768,480 | 10/1973 | Meser et al. | 604/379 |
| 4,223,677 | 9/1980 | Anderson | 604/378 |
| 4,397,644 | 8/1983 | Matthews et al. . | |
| 4,480,000 | 10/1984 | Watanabe et al. . | |
| 4,519,799 | 5/1985 | Sakurai et al. . | |
| 4,560,372 | 12/1985 | Pieniak . | |
| 4,627,848 | 12/1986 | Lassen et al. | 604/370 |
| 4,652,484 | 3/1987 | Shiba et al. . | |
| 4,673,402 | 6/1987 | Weisman et al. | 604/378 |
| 4,725,473 | 2/1988 | Van Gompel et al. . | |
| 4,755,178 | 7/1988 | Insley et al. | 604/358 |
| 4,767,586 | 8/1988 | Radwanski et al. . | |
| 4,781,962 | 11/1988 | Zamarripa et al. . | |
| 4,798,603 | 1/1989 | Meyer et al. . | |
| 4,822,668 | 4/1989 | Tanaka et al. | 604/374 |
| 4,824,596 | 4/1989 | Kitano et al. . | |
| 4,837,078 | 6/1989 | Harrington . | |
| 4,842,596 | 6/1989 | Kielpikowski et al. . | |
| 4,846,824 | 7/1989 | Lassen et al. . | |
| 4,846,842 | 7/1989 | Connolly et al. . | |
| 4,882,668 | 11/1989 | Schmid et al. . | |
| 4,883,707 | 11/1989 | Newkirk . | |
| 4,886,697 | 12/1989 | Perdelwitz, Jr. et al. . | |
| 4,892,534 | 1/1990 | Datta et al. . | |
| 4,892,598 | 1/1990 | Stevens et al. . | |
| 4,931,357 | 1/1990 | Marshall et al. . | |
| 5,004,579 | 4/1991 | Wislinski et al. . | |
| 5,033,172 | 7/1991 | Harrington | 428/373 |
| 5,045,387 | 9/1991 | Schmalz | 428/375 |
| 5,057,357 | 10/1991 | Winebarger . | |

FOREIGN PATENT DOCUMENTS

| | | |
|---|---|---|
| 0157649 | 9/1985 | European Pat. Off. . |
| 0159671 | 10/1985 | European Pat. Off. . |
| 0175481 | 3/1986 | European Pat. Off. . |
| 0210968 | 4/1987 | European Pat. Off. . |
| 0254476 | 1/1988 | European Pat. Off. . |
| 0325416 | 7/1989 | European Pat. Off. . |
| 0399511 | 11/1990 | European Pat. Off. . |
| 2087240 | 5/1982 | United Kingdom . |
| 2124907 | 2/1984 | United Kingdom . |

OTHER PUBLICATIONS

"Multi-Layer Nonwovens For Coverstock, Medical, and Other End Uses" By Jouko Pirkkanen, Nonwovens World, Nov. 1987.

"Multilayer Diaper Coverstocks Offer New Opportunities" By James E. Smith, Marketing Technical Specialist, James River Corp. Nonwovens World, Jul. 1988.

*Primary Examiner*—Randall L. Green
*Assistant Examiner*—P. Zuttarelli
*Attorney, Agent, or Firm*—John Crowe; Tara Gray; Mark D. Kuller

[57] ABSTRACT

A fluid-absorbing article for personal use, such as a diaper or incontinence pad utilizing a core component having a plurality of contiguous zones comprising (a) a zone of vulnerability arranged within said core component for maximum potential exposure to wetting and (b) a plurality of intermediate zones in direct or indirect fluid receivable relation from the zone of vulnerability in areas of reduced potential exposure to initial wetting; the corresponding core component; and a method for increasing fluid receptivity and fluid storage efficiency plus reduced rewet characteristics of core components by use of intermediate zones as described.

25 Claims, 1 Drawing Sheet

ENHANCED CORE UTILIZATION IN ABSORBENT PRODUCTS

This application is a continuation of application Ser. No. 07/768,785, filed Sep. 30, 1991, now abandoned.

The present invention relates to a fluid absorbent core component, a corresponding fluid-absorbing article utilizing such component, and to a method for more efficiently utilizing fluid-absorbing components.

BACKGROUND OF THE INVENTION

It is generally recognized that success in the marketplace, particularly with respect to fluid-absorbing articles such as disposable diapers, incontinence garments or pads and the like, depends substantially on functional efficiency, including comfort of the wearer, appearance, and price of the product being sold.

In general, such product must have an efficient fluid-retaining core component, usually comprising one or more layers of absorbent material such as wood pulp, rayon, gauze, tissue or the like, and, in some cases, superabsorbent particulate matter or powder (SAP).

To protect clothing, and surrounding areas from being wetted and stained by fluids retained in a pad or core component, such ,articles are generally backed by a fluid-impervious backing component and also usually possess a nonwoven-type fabric or coverstock material, which defines, at least, the body-contacting surface of the fluid-absorbing article. Functionally speaking, the nonwoven coverstock material, along with optional intermediate acquisition layers of defined porosity are relied on to control fluid flow and insulate the wearer from continuous contact with moisture already retained in the pad or core. The facing or coverstock must be pervious to fluids on its body-contacting side to promote rapid transfer of each fluid acquisition or insult directly into the fluid absorbent core component while, itself, remaining soft, dry and essentially nonabsorbent to aqueous fluids.

Prior art, as exemplified by Rodwanski et al. (U.S. Pat. No. 4,767,586), for instance, obtains disposable diapers from nonwoven webs of cellulosic fiber using superimposed layers of material in selected areas. This reference also proposes that webs of cellulosic fiber (i.e. for paper making) may be used in different fiber compositional areas.

U.S. Pat. No. 2,751,962 relates to a system for producing fibrous products in which coarse and fine denier fiber are incorporated into an integral web.

Marshall et at. (U.S. Pat. No. 4,931,357), relates to fibrous material from webs formed of different staple mixtures fed through separate lickerins feedably arranged in parallel axial relation over a conveyor screen or belt, the fiber feed is oriented on the belt by use of baffles to define separate lateral and vertical fiber cross-sections within the resulting web. The web, as shown, is folded over to form a cylindrical-shaped component having a homogeneous external layer.

It is now recognized that additional improvements can be achieved regarding the comfort of the wearer of such articles (a) by increasing the overall efficiency and liquid acquisition rate of the core component itself and (b) by improving fluid flow control, especially back flow or rewet properties, by varying the make up of core and/or coversheet components.

It is an object of the present invention to obtain a fluid-absorbent core component of increased receptivity and storage efficiency, plus reduced rewet characteristics.

It is a further object to obtain a core component capable of avoiding local areas of over saturation.

THE INVENTION

Figure 1:
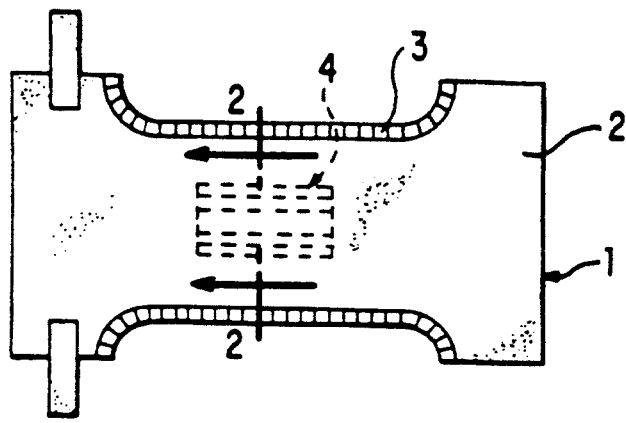
FIG. 1 is an overview of the absorbing article in diaper form.

The above objects, particularly obtaining more efficient fluid-absorbing articles such as disposable diapers, incontinence garments or pads and the like, are realized by utilizing a unique fluid-retaining core component having a plurality of zones, and arranged within at least a fluid-permeable coverstock and fluid-impervious backing layer, the core component comprising a plurality of zones defined as (a) a zone of vulnerability arranged within the core component for maximum potential exposure to initial wetting, such zone of vulnerability having, as a primary absorbent material, a wadding component comprising synthetic fiber or filament such as polyester and/or polyolefin-containing fiber inclusive of polypropylene and/or dense polyethylene, in an "effective amount", here defined as about 25%–100% and preferably 50%–100% based on zone weight. The zone of vulnerability can also include, as desired, up to about 75% of additional fiber component(s) having a higher fiber surface area and a lower volume, such as cellulose-based fiber optimally modified with superabsorbent material. A useful combination, for example, can include a polyolefin/cellulose-based staple fiber mixture having a ratio, by weight, of about 100%–50%/0%–50% optionally inclusive of one or more fibrillated film and up to about 10% of superabsorbent powder or particulate material (SAP).

The above-defined zone of vulnerability is further usefully characterized (1) by having a greater average pore size or radius and a greater liquid-solid contact angle than the average pore size and contact angle of additional (intermediate) and more wettable core zones arranged in direct or indirect fluid-receivable relation from such zone of vulnerability; and (2) by utilizing synthetic fiber or filament having an average numerical fractional value of fiber volume-to-fiber-surface area V/S (e.g. $cc/cm^2$) higher than the corresponding V/S value within wadding component(s) of intermediate core zones arranged in direct or indirect fluid-receivable relation to the zone of vulnerability; and (b) a plurality, inclusive of about 2–10 and preferably 2–5 additional intermediate core zones, arranged in core areas of reduced potential exposure to initial wetting and in direct or indirect fluid-receivable relation from the zone of vulnerability;

wherein the numerical fractional value (V/S), the average pore size or radius and the liquid-solid contact angle within wadding components of individual additional (intermediate) core zones decrease or shrink in value in general proportion to increased geometric distances from the zone of vulnerability and in general proportion to a decreased potential exposure of each intermediate zone to initial wetting.

For purposes of the present invention, the V/S fiber or fibrillated film value of the zone of vulnerability within the above-indicated parameters can vary from about 1 cc/20,000 cm$^2$ to about 1 cc/500 cm$^2$ or higher, and the corresponding V/S value within corresponding additional (intermediate) zones can usefully vary number-wise from about 1 cc/25,000 cm$^2$ to about 1 cc/40,000 cm$^2$ or lower.

A suitable fluid absorbent wadding component within the zone of vulnerability, for present purposes, comprises up to about 100% by weight of homogeneous or mixed monocomponent and/or bicomponent synthetic fiber or filament, usefully one having an average denier per filament (dpf) value within a range of about 10.0–40.0 dpf and wadding components within the fluid receivable intermediate core zones comprise fiber or filaments having average dpf values within a range of about 2.0–40 dpf. Such fiber may be monocomponent and/or bicomponent and crimped or uncrimped, as desired. The term "denier," for present purposes, connotes an art-recognized measure of filament or thread thickness expressed as grams/9000 meter length.

The instant invention is further demonstrated in the accompanying figures of which FIG. 1 is an overview of a fluid absorbing personal article in the general form of an open diaper, showing a core component (4) in hidden outline, a coversheet, leg seal components, and adhesive tabs. The fluid-impervious backing component is not shown in the figure.

Figure 2:
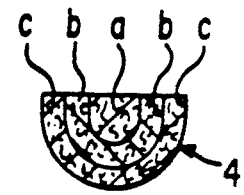
FIGS. 2, 3, and 4 are cross-sections of variations of the core along line 2—2 of FIG. 1.
Figure 3:
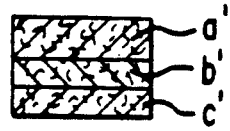
Figure 4:
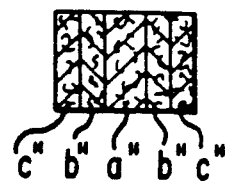

FIGS. 2–4 represent diagrammatic cross-sections of several suitable variations of core component (4) taken along line 2—2 of FIG. 1, in which the respective zones of vulnerability are respectively (a), (a'), (a''), and the respective intermediate zones (bc), (b'c'), and (b'', c''), follow the above parameters by having progressively decreased V/S values, pore size and liquid contact angles relative to the zone of vulnerability; this is obtained, for instance, by varying the fiber mix so as to lower the average dpf of the synthetic fiber and increase the concentration of one or more supplemental fibers, preferably fiber(s) having a lower average volume and a higher average fiber surface area, such as a cellulose-based fiber. The above-named zones are shown in suitable, semi-concentric configuration (FIG. 2), in stacked configuration (FIG. 3), and in vertical/contiguous configuration (FIG. 4).

Figure 5A:
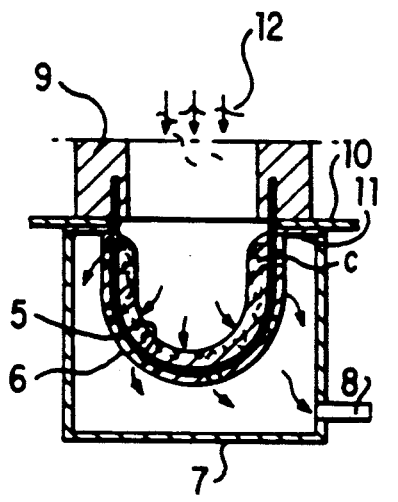
FIGS. 5a, 5b, and 5c show progressive steps of forming core zones of the variation of FIG. 2.
Figure 5B:
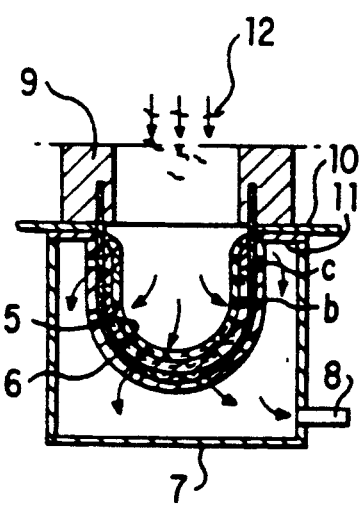
Figure 5C:
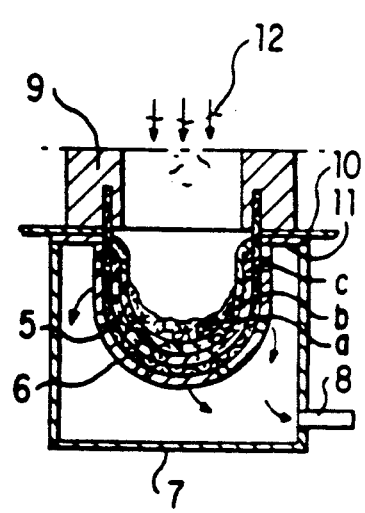

FIGS. 5A–5C exemplify progressive steps or stations representing a suitable technique for forming core zones of the FIG. 2 type having zones of different porosity, fiber mixes, V/S values and wetting angles.

Looking to the above figures in further detail, FIG. 1 represents a top schematic view of an opened diaper (1) showing a fluid-permeable nonwoven cover sheet (2), preferably one formed from a plurality of bonded polyolefin resin fiber and/or fibrillated film containing webs (not shown) such as treated polypropylene or polyethylene staple including copolymers and having homogeneous and/or mixed dpf/fiber values of a mono- and/or bicomponent-type fiber. Heat-sealed or cemented thereto is a highly hydrophobic water-impermeable leg seal component or cuff (3), preferably a topically treated polyolefin nonwoven material, and a core component (4) visible through non-woven cover sheet (2), preferably in a rectangular or oval form.

FIG. 2 schematically represents a cross-section of the core taken along line 2—2 of FIG. 1, in which "(a)" represents a centrally located zone of vulnerability, preferably one containing about 50%–100% of a synthetic thermoplastic fiber preferably topically or otherwise treated for working and retained hydrophilic properties (described below). Such fiber, as above noted, can be a spun and treated polyolefin resin, resin mix and/or copolymer(s) thereof (i.e. PP/PE) having relatively high average dpf values within the above-indicated range, and combined with about 0%–75% by zone weight of cellulose based-fiber and/or SAP powder or particulate material as above described.

As also earlier stated, the core component is normally utilized in the form of a rectangular or oval-shaped body of loosely bonded (or unbonded) wadding, comprising fiber bundles, slivers, fibrillated film and the like, of limited structural strength.

Intermediate core zones, (b) and (c) of FIG. 2, in that order, represent individual homogeneous zones arranged semiconcentrically and comprising fibrous absorbent material having a progressively smaller average fiber volume and higher average fiber surface area and a progressively smaller average pore size and liquid contact angle as the relative geometric distance from zone "(a)" increases laterally. Zones (a) (b) (c) can be individually bonded (or unbonded), or bonded "in toto" using conventional bonding techniques.

FIGS. 3–4 represent cross-sections of acceptable modifications in configuration of the zones of vulnerability relative to a plurality (shown here as two) intermediate zones demonstrated by horizontally stacked and vertically-sandwiched core zones, the primed identifying letters in FIGS. 3 and 4 being identical to or corresponding essentially to unprimed zone components (a)-(c) in FIG. 2. If desired, the number of intermediate zones can be conveniently increased to 6 or more.

FIG. 5A represents, in schematic cross-section, a step or stage in a process suitable for producing zoned core components within the scope of the present invention, in which a continuous flexible screen or belt (5) is supported from movable support elements (9) having endwise attached flanges (10) slideably resting on corresponding support flanges (11) at the top of a "U" shaped perforated forming trough (6) forming an upper surface of suction box (7). As shown, one core layer, corresponding, for instance, to intermediate core zone "(c)" of FIG. 2 has been formed from an air entrained fiber mix (12) supplied from above (see arrows) through twin lickerins axially arranged in machine direction and a mixing zone (not shown). The entrained fiber etc. is shown to be adhered to the corresponding "U" shaped flexible screen or belt (5) with the aid of a partial vacuum obtained through vacuum exhaust pipe (8) on the reverse side of the belt and trough (6).

An intermediate core component, here represented in FIG. 5B as layer "(b)", is conveniently applied at a downstream station, using different fiber, or fiber/particulate mixtures to obtain a core component of higher fiber volume and lower fiber surface area (i.e., a numerically higher V/S value) and a larger average pore size or radius and contact angle than laid down as zone (c).

FIG. 5C schematically represents a cross-section at a further downstream station in which the zone of vulnerability or "(a)" core zone is being formed. As shown, the air-entrained fiber and/or particulate matter making up such zone is applied from above in the general manner of the previous upstream stations represented by FIGS. 5A and 5B, however, the (a) core component can also be separately laid down "in toto" as a compiled fiber or filament mass as webs, or even as fibrillated film, and the entire wadding optionally bonded together using sonic, thermal, laser or similar conventional bonding techniques (not shown).

For purposes of the present invention, the term "synthetic fiber" and particularly hydrophobic fiber such as polyolefin fiber or fibrillated film, forming core elements within the present invention, is defined as fiber or filament modified for conventional processing steps (i.e. cutting, crimping and carding) and for control of flow-through properties, by topical treatment with modifiers or by the inclusion of suitable modifiers within the spun melt itself to increase hydrophilic and/or antistatic properties. Such fiber processing is disclosed, for instance, in U.S. Pat. No. 5,033,172 of James H. Harrington in which one or more N,N-polyalkoxylated 10–22 carbon fatty amines with up to 60% 10–22 carbon fatty acid amides are incorporated in the spun melt, and/or treated in accordance with U.S. Pat. No. 5,045,387 of A. C. Schmalz, in which an effective amount of a modifier composition comprising at least one of (a) a component containing alkoxylated ricinoleate with up to about 15%, by weight of modifier composition, of an 18 carbon fatty acid;

(b) a corresponding hydrogenated derivative of (a); and (c) a polyalkoxylated polydimethylsiloxane, having up to about 80% by weight of modifier composition, of one or more of component (a), (b), or combination thereof is topically applied onto hydrophobic polyolefin fiber or corresponding fibrillated film.

Also useful, for proposes of the present invention, is the above-indicated incorporation of strategically positioned art-recognized superabsorbent powder or particulate material within core zone components to improve liquid transport and favor more even and rapid distribution of fluids. Such components are typically synthesized by the polymerization of acrylic acid, acrylate esters, vinyl alcohol, ethylene oxide, acrylamide, and other vinyl monomers, or are natural absorbents such as guar gum, xanthan gum, or chitin.

One of numerous commercially available products of this type includes Sumikagel ® S—50 (a product of Sumitomo Company).

EXAMPLE 1

A. Three test diaper cores, identified as T-1, T-2 and T-3 and having the general radial or semiconcentric configuration as described in FIG. 2, are formed from sequentially-applied mixtures of air entrained 18 dpf (0.75 inch staple) polypropylene/cellulose[1] fiber at 5 separate stations onto a movable screen or belt in the manner generally described with respect to FIGS. 5A–5C. The resulting unbonded zones are sequentially laid down in about 1"-thick layers having the following concentrations (in weight percent) of polypropylene/cellulose: 0/100, 10/90, 15/85, 25/75 and 50/50 (zone of vulnerability).

[1] Georgianier Wood Pulp softwood bleached Kraft from ITT Rainier Co. hammer milled for 1 hour.

The test cores, in toto, contain 23 wt. % polypropylene staple with a density of about 0.045 g/cc. The test cores are then topped with identical polypropylene nonwoven coverstock and tested for Liquid Acquisition and Rewet characteristics (Table I) using a pressure-driven GATS (Gravimetric Absorbency Testing System) with GATS II test equipment from M/K Systems Inc. of Danvers, Mass.[2]

[2] A raised (15 cm) liquid reservoir is feedably connected by tubing (for upward flow) beneath a single-holed simple platform. The sample and a coverstock are placed thereon above the hole under 0.1 psia. A flow valve is opened for 1 second and reservoir wt. loss recorded. The difference between core uptake wt. and reservoir loss (gm) divided by time, provides initial acquisition rate data.

The rewet test is effected by obtaining an 80% core saturation using as synthetic urine a 53 dyne/cm dilute saline-surfactant[3] solution. After five minutes the test core is removed and covered with a second preweight dry bonded core and pressed (0.5 psi) for 2 minutes, the increase in weight of the dry-bonded core is reported as rewet in grams.

[3] Pluronic ® 10-R-8 surfactant from BASF Inc. Maximum unimpeded flow is 10.7 ml/second.

B. As a control, Example 1A is repeated but using identical polypropylene/cellulose staple mixtures at each zone application station to obtain uniformly-distributed fiber mix throughout the core at a density of about 0.045 gm/cc and a total content of polypropylene staple of about 23 weight percentage. The control cores, identified as C-1, C-2 and C-3, are tested for Acquisition Rate and Rewet Properties as before and the results reported in Table I below.

C. As a further control, three cores, identified as C-4, C-5 and C-6 are prepared using 100 weight percent of the same batch cellulose in each zone to obtain a core of about the same density and weight but somewhat flatter. These control cores are identically tested for Acquisition Rate and Rewet Properties and the results reported in Table I below as arithmetic averages:

TABLE I

| Core Sample # | Acquisition Rate[4] ml/second (av.) | Rewet (g) (av.) |
|---|---|---|
| T-1 | 9.7 | 7.9 |
| T-2 | | |
| T-3 | | |
| C-1 | 8.8 | 8.0 |
| C-2 | | |
| C-3 | | |
| C-4 | 8.1 | 9.9 |
| C-5 | | |
| C-6 | | |

[4]Maximum unimpeded flow is 10.7 ml/second.

EXAMPLE 2

A. Example 1A is repeated in core samples T-4, T-5 and T-6, using 15 dpf 0.75" polyester staple in place of polypropylene staple. The cores are identically tested as before and test results reported in Table II below as averages.

B. Example 2A is repeated with control cores C-7, C-8 and C-9, in which the stone total amounts of PET and identical wt. % of PET/cellulose is applied at each zone to obtain a uniform staple distribution through the cores. The cores are tested as before and test results reported in Table II below as averages.

TABLE II

| Core Sample # | Acquisition Rate*[4] ml/second (av.) |
|---|---|
| T-4 | 10.5 |
| T-5 | |
| T-6 | |
| C-7 | 8.7 |
| C-8 | |
| C-9 | |

EXAMPLE 3

Examples 1A and 1B are repeated but with the addition of 5 weight percent of Sumikagel ® S-50 (SAP) within the zone of vulnerability and 5 weight percent within the outermost zone (the first laid down in FIG. 5A). Rewet determinations are carried out as before and the test results reported in Table III as average values in comparison with Example 1A and 1B values.

TABLE III

| Core Sample # | Rewet*[4] (no SAP) (g) | Rewet (with SAP) (g) |
| --- | --- | --- |
| T-1 | 7.9 | 5.5 |
| T-2 | | |
| T-3 | | |
| C-1 | 8.0 | 6.3 |
| C-2 | | |
| C-3 | | |

I claim:

1. A fluid-absorbing article comprising, in combination, a fluid-retaining core component arranged within at least a fluid-permeable coverstock and a fluid-impervious backing layer, said core component having a plurality of zones defined as:
   (a) a zone of vulnerability positioned in said core component for maximum potential exposure to initial wetting, said zone of vulnerability having a wadding component comprising synthetic fiber or filament; and
   (b) a plurality of additional core zones in the core component each having a wadding component arranged in the core component in areas of reduced potential exposure to initial wetting and in fluid-receivable relation from said zone of vulnerability; wherein the wadding component in the zone of vulnerability has (1) a greater average pore size and a greater liquid-solid contact angle than the average pore size and contact angle of the wadding components within the plurality of additional core zones, and (2) a higher average fractional value of fiber volume-to-fiber surface area than the average fractional value of fiber volume-to-fiber surface area within the wadding components of the additional core zones; and wherein the average fractional value of fiber volume-to-fiber surface area, the average pore size and the liquid-solid contact angle within the wadding components of said additional core zones decrease in relative value in general proportion to increased geometric distance from said zone of vulnerability and corresponding decreased potential exposure to initial wetting.

2. The fluid-absorbing article of claim 1 wherein the additional core zones are in semiconcentric arrangement about said zone of vulnerability.

3. The fluid-absorbing article of claim 1 wherein the wadding component of the zone of vulnerability comprises about 25%–100% by weight of the zone of polyolefin or polyester staple fiber or filament, and at least some of said additional core zones comprise up to about 10% superabsorbent particulate matter and up to about 100% by weight of a cellulose based-fiber.

4. The fluid-absorbing article of claim 1 wherein the zone of vulnerability further comprises an additional fiber component comprising up to about 50% by weight of a cellulose-based fiber.

5. The fluid-absorbing article of claim 1 wherein the zone of vulnerability of said core component comprises fiber or filament having an average dpf value within a range of about 10.0–40.0 dpf and wadding components within the additional core zones comprise fiber or filament having average dpf values within a range of about 2.0–40 dpf.

6. The fluid-absorbing article of claim 1 wherein the wadding components in the zone of vulnerability and in the additional core zones comprise polyolefin fiber or filament spun from a spun melt comprising propylene and an active amount of a modifier composition having
   (a) at least one N,N-polyalkoxylated 10–22 carbon fatty amine, and
   (b) up to about 60%, by weight of modifier composition, of a primary or secondary 10–22 carbon fatty acid amide.

7. The fluid-absorbing article of claim 1 wherein the wadding components in the zone of vulnerability and in the additional core zones comprise polyolefin fiber or filament topically treated with an effective amount of a modifier composition, comprising at least one of
   (a) a component containing alkoxylated ricinoleate with up to about 15%, by weight of modifier composition, of an 18 carbon fatty acid;
   (b) a corresponding hydrogenated derivative of component (a); and
   (c) a polyalkoxylated polydimethylsiloxane, having up to about 80% by weight of modifier composition, of one or more of component (a), (b), or combination thereof.

8. The fluid-absorbing article of claim 1 wherein the zone of vulnerability and additional core zones contain superabsorbent particulate matter.

9. The fluid-absorbing article of claim 1 wherein at least one additional core zone is bonded to at least one adjacent additional core zone.

10. The fluid-absorbing article of claim 1 wherein the zone of vulnerability and additional core zones are bonded together.

11. The fluid-absorbing article of claim 1 wherein at least one of said additional core zones are in lateral contact with said zone of vulnerability.

12. A core component for use in fluid-absorbing article for personal use comprising, in combination:
   (a) a zone of vulnerability positioned in said core component for maximum potential exposure to initial wetting, said zone of vulnerability having a wadding component comprising synthetic fiber or filament; and
   (b) a plurality of additional core zones in the core component each having a wadding component arranged in the core component in areas of reduced potential exposure to initial wetting and in fluid-receivable relation from said zone of vulnerability; wherein the wadding component in the zone of vulnerability has (1) a greater average pore size and a greater liquid-solid contact angle than the average pore size and contact angle of the wadding components within the plurality of additional core zones, and (2) a higher average fractional value of fiber volume-to-fiber surface area than the average fractional value of fiber volume-to-fiber surface area within the wadding components of the additional core zones; and wherein the average fractional value of fiber volume-to-fiber surface area, the average pore size and the liquid-solid contact angle within the wadding components of said additional core zones decrease in relative value in general proportion to increased geometric distance from the zone of vulnerability and corresponding decreased potential exposure to initial wetting.

13. The core component of claim 12 wherein said additional core zones are in semi-concentric arrangement about said zone of vulnerability.

14. The core component of claim 12 wherein the zone of vulnerability of said core component comprises fiber or filament having a dpf value within a range of about 10.0–40.0 and the wadding components within the additional core zones comprise fiber having dpf values within a range of 2.0–40 dpf.

15. The core component of claim 12 wherein the wadding components in the additional core zones comprise polyolefin fiber or filament spun from a spun melt comprising polypropylene and an active amount of a modifier composition having (a) at least one N,N-polyalkoxylated 10–22 carbon fatty amine, and (b) up to about 60% by weight of modifier composition of a primary or secondary fatty acid amide.

16. The core component of claim 12 wherein the wadding components in the additional core zones comprise polyolefin fiber or filament topically treated with an effective amount of a modifier composition comprising at least one of (a) a component containing alkoxylated ricinoleate with up to about 15%, by weight of modifier composition, of an 18 carbon fatty acid;

(b) a corresponding hydrogenated derivative of component (a); and (c) a polyalkoxylated polydimethylsiloxane, having up to about 80% by weight of modifier composition of one or more of component (a), (b), or combination thereof.

17. The core component of claim 12, wherein the zone of vulnerability further comprises an additional fiber component comprising about 50% by weight of a cellulose-based fiber or particulate matter.

18. The core component of claim 12 wherein at least some of said additional core zones are in lateral contact with said zone of vulnerability.

19. The core component of claim 12 wherein the wadding component of the zone of vulnerability comprises up to about 50%–100% by weight of polyolefin or polyester staple fiber or filament, and the wadding components of each additional core zones individually comprise up to about 100% by weight of a cellulose based-fiber and up to about 10% superabsorbent particulate matter.

20. The core component of claim 19 wherein the zone of vulnerability further comprises an additional fiber component comprising up to about 50% by weight of cellulose-based fiber.

21. The core component of claim 12 wherein the fiber or filament comprising the wadding components within the zone of vulnerability and additional core zones are of constant length.

22. The core component of claim 21 wherein the wadding component in the zone of vulnerability comprises about 25%–100% by weight of polyolefin or polyester staple fiber or filament and wherein a wadding component in an additional core zone furthest in geometric distance from the zone of vulnerability comprises up to 100% by weight of cellulose-based fiber and the remaining balance by weight of superabsorbent material.

23. The core component of claim 21 wherein the zone of vulnerability further comprises an additional fiber component comprising up to about 50% by weight of a fiber having a higher fiber surface area and a lower fiber volume than the fiber or filament in the wadding component of the zone of vulnerability.

24. The core component of claim 23 wherein the additional fiber component comprises cellulose-based fibers.

25. The core component of claim 12 wherein both the zone of vulnerability and intermediate zones contain superabsorbent powder.

* * * * *